(12) United States Patent
Park et al.

(10) Patent No.: US 10,338,370 B2
(45) Date of Patent: Jul. 2, 2019

(54) CLOCK SIGNAL GENERATORS AND SUBSTRATE INSPECTING APPARATUSES HAVING THE SAME

(71) Applicant: Samsung Electronics Co., Ltd., Suwon-si, Gyeonggi-do (KR)

(72) Inventors: Jun-Bum Park, Goyang-si (KR); Kyung-Sik Kang, Bucheon-si (KR); Tae-Joong Kim, Hwaseong-si (KR); Sang-Ok Seok, Seongnam-si (KR); Byeong-Hwan Jeon, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 238 days.

(21) Appl. No.: 15/377,070

(22) Filed: Dec. 13, 2016

(65) Prior Publication Data
US 2017/0336616 A1 Nov. 23, 2017

(30) Foreign Application Priority Data
May 17, 2016 (KR) .................. 10-2016-0059990

(51) Int. Cl.
| | | |
|---|---|---|
| G02B 21/36 | (2006.01) | |
| G01N 21/95 | (2006.01) | |
| G01N 21/88 | (2006.01) | |
| G02B 26/10 | (2006.01) | |
| G02B 21/00 | (2006.01) | |

(52) U.S. Cl.
CPC ....... *G02B 21/365* (2013.01); *G01N 21/8806* (2013.01); *G01N 21/8851* (2013.01); *G01N 21/9501* (2013.01); *G02B 21/0096* (2013.01); *G02B 26/105* (2013.01)

(58) Field of Classification Search
CPC ................ G02B 21/365; G02B 26/105; G02B 21/0096; G01N 21/8806; G01N 21/8851; G01N 21/9501
USPC ......................................... 348/79
See application file for complete search history.

(56) References Cited

U.S. PATENT DOCUMENTS

| | | | |
|---|---|---|---|
| 4,420,760 A | 12/1983 | Phillips | |
| 4,528,448 A | 7/1985 | Doggett | |
| 4,837,588 A * | 6/1989 | Imakawa | G06K 15/1219 250/235 |

(Continued)

FOREIGN PATENT DOCUMENTS

| | | |
|---|---|---|
| JP | 2007164061 A | 6/2007 |
| KR | 19970060095 | 8/1997 |

(Continued)

*Primary Examiner* — Zaihan Jiang
(74) *Attorney, Agent, or Firm* — Harness, Dickey & Pierce, P.L.C.

(57) ABSTRACT

A clock signal generator includes an optic mirror rotatable to scan an incident light beam in a first direction, a grid plate including a plurality of grid arrays arranged in a second direction different from the first direction, wherein light reflected from the optic mirror is selectively passed through when the light beam is scanned on the grid plate in the first direction, the grid array being offset in the first direction by a particular distance with respect to an adjacent grid array, a light detector configured to detect a light passing through the grid arrays, and a pixel clock generator configured to generate a clock signal based on detection signals received from the light detector.

18 Claims, 10 Drawing Sheets

(56) References Cited

U.S. PATENT DOCUMENTS

| | | | | |
|---|---|---|---|---|
| 4,962,431 A * | 10/1990 | Imakawa | ............ | G06K 15/1219 358/296 |
| 5,081,477 A * | 1/1992 | Gibson | .............. | G06K 15/1219 250/236 |
| 5,095,315 A * | 3/1992 | Takeyama | .......... | G06K 15/1219 347/235 |
| 5,122,678 A * | 6/1992 | Takeyama | .......... | G06K 15/1219 327/156 |
| 5,218,195 A * | 6/1993 | Hakamata | .............. | B82Y 15/00 250/216 |
| 5,294,944 A * | 3/1994 | Takeyama | .............. | H04N 1/502 347/232 |
| 5,445,556 A * | 8/1995 | Miura | .................... | B24B 19/02 451/28 |
| 5,446,556 A * | 8/1995 | Kuroiwa | .............. | H04N 1/0283 250/236 |
| 5,812,629 A | 9/1998 | Clauser | | |
| 6,493,019 B1 * | 12/2002 | Hirasawa | ............... | H04N 1/053 347/232 |
| 6,742,133 B2 | 5/2004 | Saeki | | |
| 8,718,228 B2 | 5/2014 | Nakamura et al. | | |
| 8,885,145 B2 | 11/2014 | Sandstrom | | |
| 9,105,369 B2 | 8/2015 | Koehler | | |
| 2001/0020676 A1* | 9/2001 | Nakaya | .................. | G03F 7/2055 250/234 |
| 2004/0146295 A1* | 7/2004 | Furman | .............. | G01N 21/8806 398/9 |
| 2006/0071075 A1* | 4/2006 | Moon | .................. | G06K 7/1094 235/454 |
| 2011/0001888 A1* | 1/2011 | Brown | .................. | G02B 26/085 348/744 |
| 2013/0120563 A1 | 5/2013 | Terada et al. | | |

FOREIGN PATENT DOCUMENTS

| | | |
|---|---|---|
| KR | 100405020 B1 | 11/2003 |
| KR | 20110089449 A | 8/2011 |
| KR | 20130092429 A | 8/2013 |
| KR | 20150035035 A | 4/2015 |

* cited by examiner

CLOCK SIGNAL GENERATORS AND SUBSTRATE INSPECTING APPARATUSES HAVING THE SAME

CROSS-REFERENCE TO RELATED APPLICATIONS

This application claims priority under 35 U.S.C. § 119 to Korean Patent Application No. 10-2016-0059990, filed on May 17, 2016 in the Korean Intellectual Property Office (KIPO), the contents of which are herein incorporated by reference in their entirety.

BACKGROUND

1. Field

Some example embodiments relate to clock signal generators and substrate inspecting apparatuses having the same. More particularly, some example embodiments relate to a clock signal generators configured to generate a high-speed pixel clock signal in laser scanner based inspection systems and substrate inspecting apparatuses having the same.

2. Description of the Related Art

A laser scanner based inspection apparatus may use a high-speed scanner device to generate an image. Examples of high-speed scanner devices include a galvanometric mirror, a polygon mirror, etc. These scanner devices may use gratings to generate a pixel clock signal, providing a way to correct image distortions due to a nonlinear scanning speed.

However, in order to obtain an image of high resolution, when a grating period (pitch) is decreased, signal contrast according to diffraction limit may be deteriorated, thereby causing difficulties in generating a high-speed pixel clock.

SUMMARY

Example embodiments provide a clock signal generator capable of obtaining an image of high resolution.

Example embodiments provide a substrate inspecting apparatus including the above clock signal generator.

According to some example embodiments, a clock signal generator, may include: an optic mirror configured to be rotated to scan an incident first light beam in a first direction based on reflecting the first light beam; a grid plate including a plurality of grid arrays arranged in a second direction different from the first direction, the grid plate configured to selectively direct at least a portion of the reflected first light beam through the grid arrays when the first light beam is scanned over the grid plate in the first direction, each grid array, of the plurality of grid arrays, being offset in the first direction by a particular distance with respect to an adjacent grid array of the plurality of grid arrays; a light detector configured to generate detection signals based on detecting portions of the first light beam passing through the grid arrays; and a pixel clock generator configured to generate a clock signal based on the detection signals.

According to some example embodiments, a clock signal generator, may include: an optic mirror configured to be rotated to scan a first light beam in a first direction; a light source configured to generate the first light beam and direct the first light beam to the optic mirror; a grid plate including N grid arrays, N being a natural number, arranged in a second direction different from the first direction, each grid array of the plurality of grid arrays configured to selectively pass a portion of the first light beam reflected from the optic mirror therethrough when the optic mirror scans the first light beam on the grid plate in the first direction, each grid array including a plurality of slits spaced apart from each other by a particular pitch (P), each grid array being offset in the first direction by (1/N)*pitch (P) with respect to an adjacent grid array of the plurality of grid arrays; a light detector configured to generate detection signals based on detecting portions of the first light beam passing through the grid arrays; and a pixel clock generator configured to generate a clock signal based on the detection signals.

According to example embodiments, a substrate inspecting apparatus may include: a stage configured to support a substrate; an optic mirror configured to be rotated and including a first reflective surface and a second reflective surface, the optic mirror configured to be rotated to cause the first reflective surface to scan a reflected first light beam in a first direction and to cause the second reflective surface to scan a reflected second light beam in a second direction on the substrate; a clock signal generator including a grid plate including a plurality of grid arrays arranged in a third direction different from the first direction, the grid arrays configured to selectively pass a portions of the reflected first light beam therethrough when the first reflective surface scans the first light beam on the grid plate in the first direction, each grid array being offset in the first direction by a particular distance with respect to an adjacent grid array, a light detector configured to generate detection signals based on detecting portions of the first light beam passing through the grid arrays, and a pixel clock generator configured to generate a clock signal based on the detection signals; and an image generator configured to generate an image based on detection of the second light beam reflected from the substrate through the second reflective surface.

According to some example embodiments, a substrate inspecting apparatus may use an optic mirror as a galvano mirror to scan a laser beam on a substrate and detect a light from the substrate and may obtain an image from the detected light. The substrate inspecting apparatus may include a clock signal generator which is configured to detect a rotation movement of the galvano mirror in real time and to generate a clock signal based on the measurement of the position of the galvano mirror. The clock signal generator may include multi-grid arrays of N rows with regular gratings, which are offset by a same distance.

According to some example embodiments, a clock signal generator may include: an optic mirror configured to be rotated to scan an incident first light beam in a first direction based on reflecting the first light beam; a grid plate including at least one grid array extending in the first direction, the grid plate configured to selectively direct at least a portion of the reflected first light beam through the grid plate when the optic mirror scans the first light beam over the grid plate in the first direction; a light detector configured to generate detection signals based on detecting portions of the first light beam passing through the grid plate; and a pixel clock generator configured to generate a clock signal based on the detection signals.

Accordingly, image distortions due to nonlinear movement characteristics of the galvano mirror may be limited and/or prevented from occurring and thus an image having an improved resolution may be obtained. Additionally, a high-speed pixel clock signal may be generated even in the case of below a limit pitch of diffraction grating according to a wavelength of a laser beam.

BRIEF DESCRIPTION OF THE DRAWINGS

Example embodiments will be more clearly understood from the following detailed description taken in conjunction with the accompanying drawings. FIGS. 1 to 14 represent non-limiting, example embodiments as described herein.

FIG. 1 is a block diagram illustrating a substrate inspecting apparatus in accordance with some example embodiments.

FIG. 2 is a perspective view illustrating a portion of a clock signal generator in FIG. 1.

FIG. 4 is a perspective view illustrating a portion of a grid plate of the clock signal generator in FIG. 2.

FIG. 5 is a plan view illustrating the grid plate in FIG. 4.

FIG. 6 is a side view illustrating a grid plate and a light detector in FIG. 2.

FIG. 7 is a block diagram illustrating the light detector of the clock signal generator in FIG. 2 and a pixel clock generator.

FIG. 8 is a block diagram illustrating a light detector and an image signal processor in FIG. 1.

FIG. 9 is a plurality of graphs illustrating detection signals outputted from the light detector in FIG. 7 and a pixel clock signal generated by merging the detection signals.

FIG. 10 is a plan view illustrating a grid plate of a clock signal generator in accordance with some example embodiments.

FIG. 11 is a side view illustrating the grid plate in FIG. 10 and a light detector.

FIG. 12 is a plan view illustrating a grid plate of a clock signal generator in accordance with some example embodiments.

FIG. 13 is a side view illustrating the grid plate in FIG. 12 and a light detector.

FIG. 14 is a flow chart illustrating a substrate inspecting method in accordance with some example embodiments.

DETAILED DESCRIPTION OF EXAMPLE EMBODIMENTS

Figure 1:
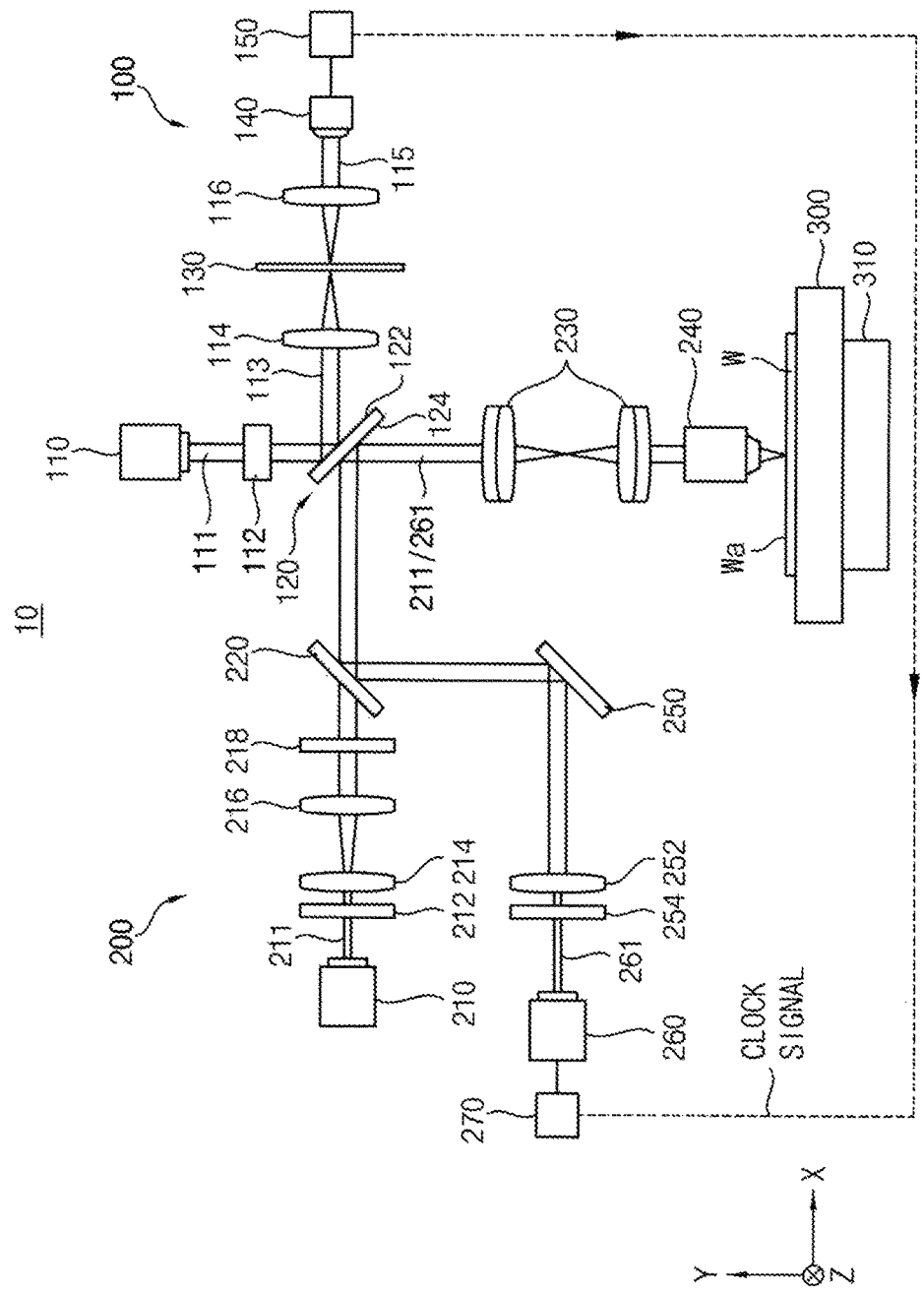
Figure 2:
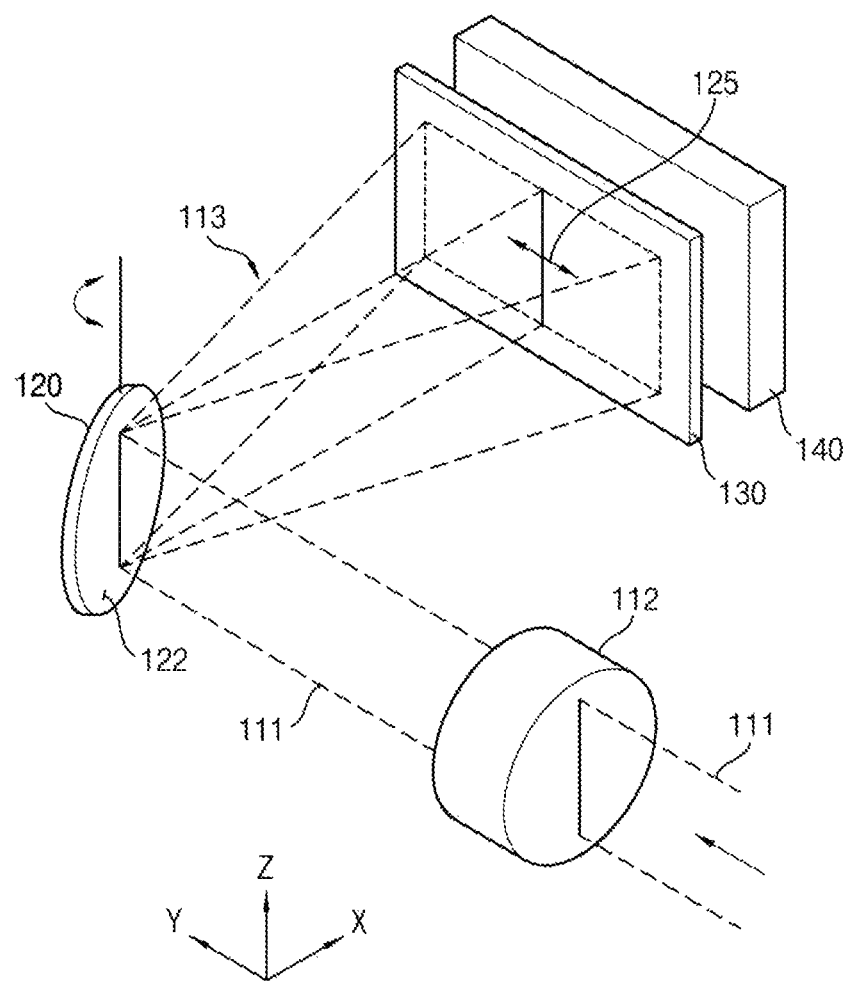
Figure 3A:
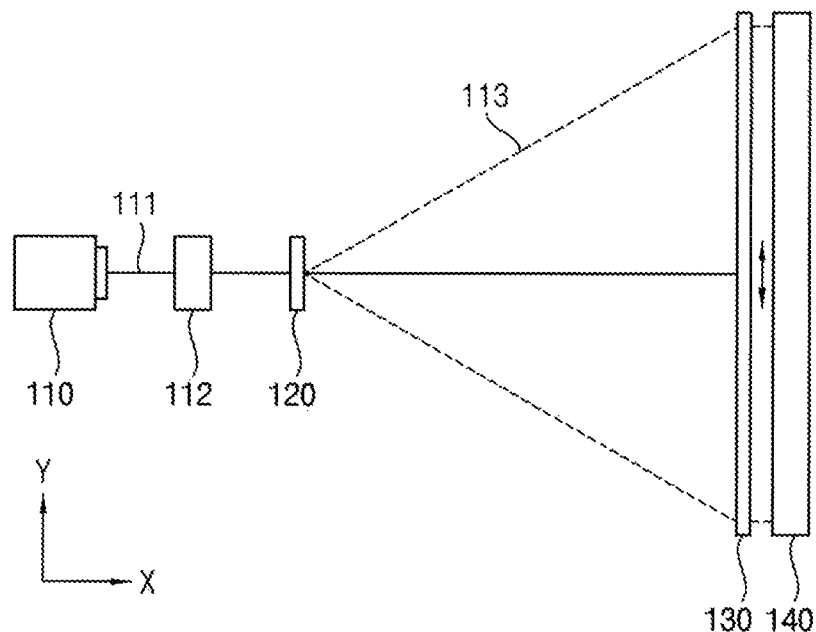
FIG. 3A is a plan view of a measurement beam passing through an optic mirror of the clock signal generator in FIG. 2.
Figure 3B:
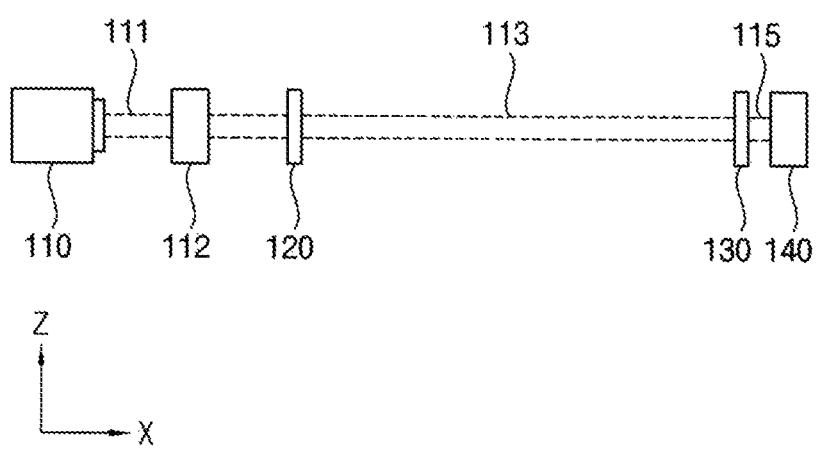
FIG. 3B is a side view illustrating the measurement beam in FIG. 3A.
Figure 4:
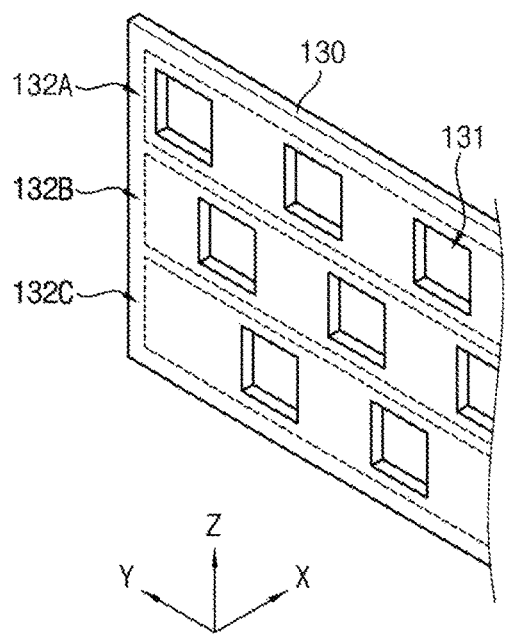
Figure 5:
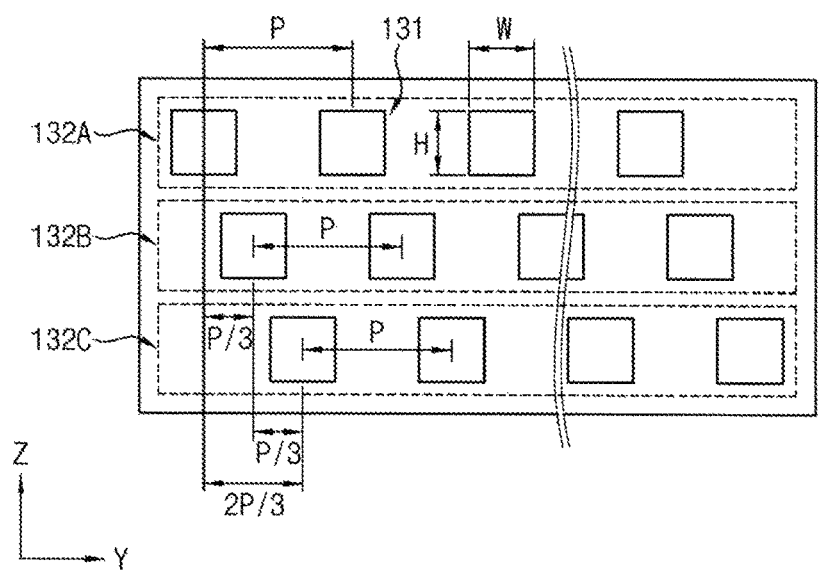
Figure 6:
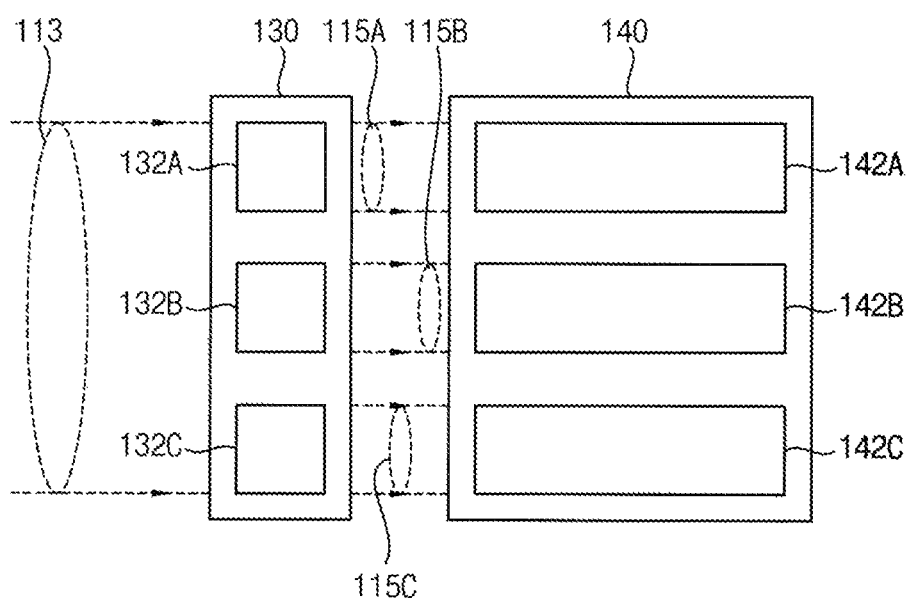
Figure 7:
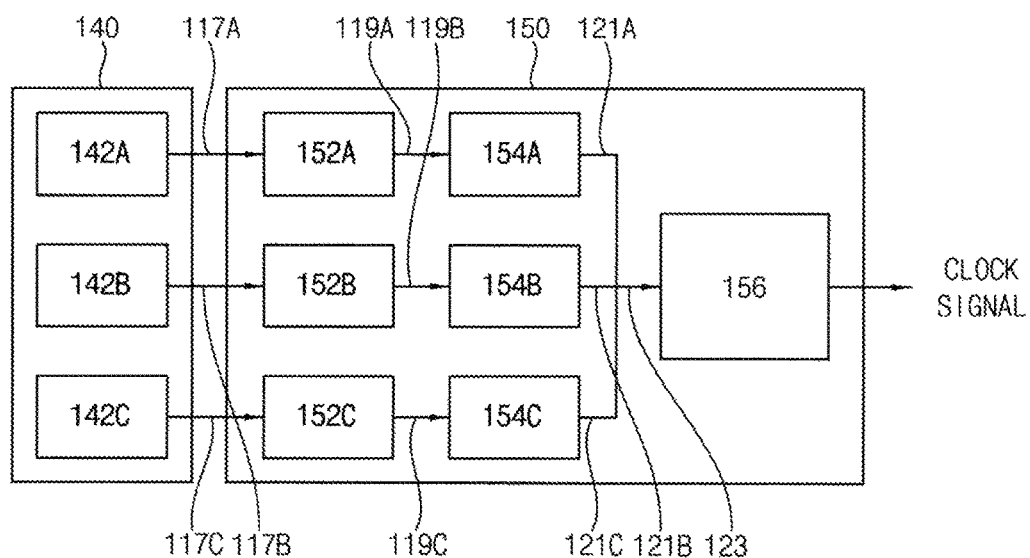
Figure 8:
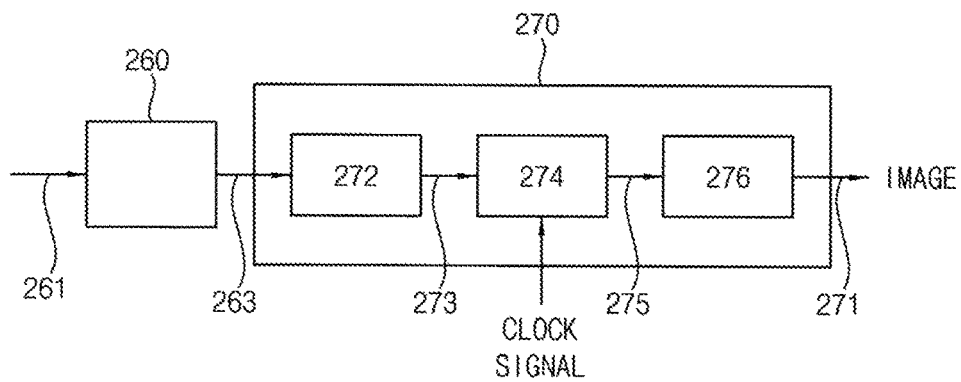

FIG. 1 is a block diagram illustrating a substrate inspecting apparatus in accordance with some example embodiments. FIG. 2 is a perspective view illustrating a portion of a clock signal generator in FIG. 1. FIG. 3A is a plan view of a measurement beam passing through an optic mirror of the clock signal generator in FIG. 2. FIG. 3B is a side view illustrating the measurement beam in FIG. 3A. FIG. 4 is a perspective view illustrating a portion of a grid plate of the clock signal generator in FIG. 2. FIG. 5 is a plan view illustrating the grid plate in FIG. 4. FIG. 6 is a side view illustrating a grid plate and a light detector in FIG. 2. FIG. 7 is a block diagram illustrating the light detector of the clock signal generator in FIG. 2 and a pixel clock generator. FIG. 8 is a block diagram illustrating a light detector and an image signal processor in FIG. 1. In all figures in this specification, a direction indicated by an arrow and a reverse direction thereof are considered as the same direction.

Referring to FIGS. 1 to 8, a substrate inspecting apparatus 10 may include a clock signal generator 100, an image generator 200, and a stage 300 configured to support a substrate as an object to be inspected. The clock signal generator 100 may detect a light scanning by a first reflective surface 122 of an optic mirror 120 to generate a clock signal. The image generator 200 may scan a light beam onto the substrate by a second reflective surface 124 of the optic mirror 120 and detect a reflected light beam from the substrate surface, and process an image signal from the detected light in accordance with the clock signal to generate an image of the substrate surface.

In some example embodiments, a semiconductor wafer W may be supported on the stage 300. The substrate inspecting apparatus 10 may include a drive mechanism 310 configured to move the stage 300. The stage 300 may be moved in X direction and/or the Z direction by the drive mechanism 310. Additionally, the stage 300 may be moved in the Y direction by the drive mechanism 310 to place an upper surface Wa of the semiconductor wafer W in a focus position. In FIG. 1, the left and right directions on the paper are referred to as X direction, the vertical direction to the plane of the paper is referred to as Y direction, and the up and down directions on the paper are referred to as Z direction.

In some example embodiments, the substrate inspecting apparatus 10 may use a light scanner as a deflector of a light beam emitted from a light source to scan the light beam on the upper surface Wa of the wafer W to generate an image of the upper surface Wa. The light beam may be associated with one or more specific wavelengths and phases, benefits for high power, etc. In some example embodiments, the light source is a laser source, such that the light beam generated by the light source is a laser beam.

The light scanner may include an optic mirror 120. The optic mirror 120 may include a galvano mirror. For example, the optic mirror 120 may be connected to a drive shaft of an electric motor, such that the optic mirror 120 is configured to be rotatably adjusted by the electric motor. The optic mirror 120, which may be configured to deflect and/or reflect incident light beams through one or more angles in accordance, based on an electric signal supplied to the electric motor connected to the optic mirror 120, may be used to deflect the laser beam.

The optic mirror 120 may have a first reflective surface 122 configured to scan a light beam in a first direction (Y direction) on ("over") a grid plate 130 of the clock signal generator 100 and a second reflective surface 124 configured to scan a light beam in a second direction (X direction) on the wafer W, based on rotation of the optic mirror 120. For example, the first reflective surface 122 and the second reflective surface 124 may be provided on both sides (e.g., opposite sides) of the optic mirror 120, respectively.

In some example embodiments, the clock signal generator 100 may include a first light source 110 (e.g., light emitter, light beam source, etc.), a light scanner including the optic mirror 120, the grid plate 130, a light detector 140, and a pixel clock generator 150.

The first light source 110 may include a first light source configured to generate a light beam 111 as a clock signal generating light beam. The first light source 110 may include a first laser source configured a laser beam as the clock signal generating light beam. The light beam 111 emitted from the first light source 110 may be directed to be incident on the first reflective surface 122 of the optic mirror 120 by a light source optical system 112.

For example, the first light source 110 may generate a light beam 111 that is a linear laser beam as a linear light source. In another example, the first light source 110 may generate a light beam 111 that is a laser beam as point light source, and the light source optical system 112 may transform the laser beam of the point light source into a linear light beam having a cross section extending in a particular direction as a linear band and may direct the transformed linear laser beam to the first reflective surface 122 of the optic mirror 120. Accordingly, a linear laser beam emitted from the first light source 110 may be incident into the first reflective surface 122 of the optic mirror 120.

As illustrated in FIGS. 2, 3A and 3B, as the optic mirror 120 rotates, i.e., swings, through a desired (or, alternatively, predetermined) angle, the linear light beam 111 may be reflected as a reflected light beam 113 that may be scanned 125 in the first direction (Y direction) by the optic mirror 120 onto the grid plate 130. The light beam 113 scanning the grid plate 130 may include a linear light beam extending in a third direction (Z direction). The light beam 113 reflected from the first reflective surface 122 of the optic mirror 120 may be condensed on the grid plate 130 by a condenser lens 114.

Referring to FIG. 4, the grid plate 130 may include a plurality of slits 131 through which the light beam 113 may selectively pass when the light beam 111 is scanned 113 in the first direction (Y direction). The slits 131 may be arranged along the first direction (Y direction), i.e., an extending direction of the grid plate 130, to be spaced apart from each other by a desired (or, alternatively, predetermined) pitch (P). The slits 131 may be arranged in rows parallel with the first direction (Y direction) respectively. Accordingly, selected portions of the light beam 113 beam may be allowed to pass through or may be blocked by gratings of the grid plate 130 depending on the position of the optic mirror 120.

For example, the slit 131 may be an opening which penetrates through the grid plate 130. In another example, the slit 131 may be a transparent portion of the grid plate 130 and a portion between the slits 131 may be an opaque portion of the grid plate 130. In this case, the grid plate 130 may include transparent portions and opaque portions alternately arranged in the first direction (Y direction).

In some example embodiments, the grid plate 130 may include N grid arrays (where N is a natural number) arranged in a fourth direction different from the first direction (Y direction). The grid array may be shifted in the first direction (Y direction) by (1/N)*pitch (P) with respect to adjacent grid array. The adjacent grid arrays may be offset by (1/N)*pitch (P) to each other. A mth grid array (m=2, 3, . . . , N) may be shifted by (1/N)*(P) with respect to a (m−1)th grid array. The mth grid array (m=2, 3, . . . , N) may be shifted by ((m−1)/N)*(P) with respect to a first grid array.

As illustrated in FIG. 5, the grid plate 130 may include three first, second and third grid arrays 132A, 132B and 132C of slits 131 arranged in the fourth direction (Z direction) perpendicular to the first direction (Y direction).

The first grid array 132A may include slits 131 arranged in the first direction (Y direction) to be spaced apart from one another. The second grid array 132B may include slits 131 arranged in the first direction (Y direction) to be spaced apart from one another. The third grid array 132C may include slits 131 arranged in the first direction (Y direction) to be spaced apart from one another. The pitch (P) of the first grid array 132A may be the same as the pitch (P) of the second grid array 132B, and the pitch (P) of the second grid array 132B may be the same as the pitch (P) of the third grid array 132C.

The number and the pitch of the slits 131 of each of the first to third grid arrays 132A, 132B and 132C may be determined in order to achieve a maximum resolution within a diffraction limit according to the wavelength of the light beam 111. Each of the first to third grid arrays 132A, 132B and 132C may include the slits 131 of 1×n array, where n is a positive integer number. For example, each of the first to third grid arrays 132A, 132B and 132C may include about 1,500 slits 131.

The second grid array 132B may be shifted ("offset") by (⅓)*(P) with respect to the first grid array 132A. The third grid array 132C may be shifted by (⅓)*(P) with respect to the second grid array 132B. The third grid array 132C may be shifted by (⅔)*(P) with respect to the first grid array 132A.

As illustrated in FIG. 6, the light detector 140 may detect a light beam 113 passing through the grid plate 130. The light beam portions 115A-C selectively passing through the grid plate 130 based on the grid arrays 132A-C may be condensed on the light detector 140 by a condenser lens 116. The light detector 140 may include first, second and third detection arrays 142A, 142B and 142C to respectively detect light beam portions 115A-C (e.g., light beams 115A-C) passing through the first, second and third grid arrays 132A, 132B and 132C, respectively. The detection arrays 142A, 142B and 142C may include one or more photodiodes.

The first detection array 142A may output a first voltage signal representing the intensity of the light beam 115A passing through the first grid array 132A. The second detection array 142B may output a second voltage signal representing the intensity of the light beam 115B passing through the second grid array 132B. The third detection array 142C may output a third voltage signal representing the intensity of the light beam 115C passing through the third grid array 132C.

Referring to FIG. 1 and FIG. 7, the pixel clock generator 150 may generate a clock signal (CLK) based on one or more signals outputted from the light detector 140. In some example embodiments, the pixel clock generator 150 may be at least partially implemented by a processor executing program instructions stored in a memory. The pixel clock generator 150 may include at least one of a memory and a processor, where the memory stores program instructions and the processor is configured to execute the program instructions to perform at least a portion of the functionality of the pixel clock generator 150. As illustrated in FIG. 7, the pixel clock generator 150 may include first to third amplifiers 152A, 152B and 152C, first to third A/D converters 154A, 154B and 154C, and a synthesizer 156.

In particular, the first to third amplifiers 152A, 152B and 152C may amplify the first to third voltage signals 117A-C outputted from the first to third detection arrays 142A, 142B and 142C, respectively, and output the amplified signals 119A-C to the first to third A/D converters 154A, 154B and 154C, respectively. Each of the first to third A/D converters 154A, 154B and 154C may convert an analog signal to a digital signal. The first A/D converter 154A may convert the amplified first voltage signal 119A to a first digital signal 121A. The second A/D converter 154B may convert the amplified second voltage signal 119B to a second digital signal 121B. The third A/D converter 154C may convert the amplified third voltage signal 119C to a third digital signal 121C. The synthesizer 156 may merge a plurality of parallel digital input signals 121A-C to one channel signal 123. The synthesizer 156 may merge the first to third digital signals 121A-C inputted from the first to third A/D converters 154A, 154B and 154C to the one channel signal 123 to generate the clock signal CLK.

Referring back to FIG. 1, in some example embodiments, the image generator 200 may include a second light source 210, the light scanner having the optic mirror 120, an observation optical system, a light detector 260, and an image signal processor 270.

The second light source 210 may be configured to generate a light beam 211, also referred to herein as an inspecting light beam 211. The second light source 210 may be a laser source, such that the light beam 211 may be a laser beam. The light beam 211 emitted from the second light source 210 may be incident onto an objective lens 240 through the light scanner and the observation optical system to illuminate the surface of the semiconductor wafer W. A reflected light beam 261 from the surface of the semiconductor wafer W may be directed back to the objective lens 240 and further to be directed to enter the light detector 260 through the observation optical system. Then, an image generated by the image signal processor 270 based on the reflected light beam 261 may be used to inspect the surface of the semiconductor wafer W.

In some example embodiments, the light detector 260 may be at least partially implemented by a processor executing program instructions stored in a memory. The light detector 260 may include at least one of a memory and a processor, where the memory stores program instructions and the processor is configured to execute the program instructions to perform at least a portion of the functionality of the light detector 260.

In some example embodiments, the image signal processor 270 may be at least partially implemented by a processor executing program instructions stored in a memory. The image signal processor 270 may include at least one of a memory and a processor, where the memory stores program instructions and the processor is configured to execute the program instructions to perform at least a portion of the functionality of the image signal processor 270.

In particular, the light beam 211 emitted from the second light source 210 may be incident into the second reflective surface 124 of the optic mirror 120 through an aperture 212, an expanding lens 214, a condenser lens 216 and a polarizing mirror 220. The light beam 211 reflected from the second reflective surface 124 of the optic mirror 120 may be condensed on the surface Wa of the semiconductor wafer W by a relay lens 230 and the objective lens 240.

The reflected light beam 261 from the surface Wa of the semiconductor wafer W may be condensed on the light detector 260 through the objective lens 240, the relay lens 230, the polarizing mirror 220, a mirror 250, a condenser lens 252 and an aperture 254. The light detector 260 may generate an image signal 263 in proportion to the intensity of the detected light beam 261.

As illustrated in FIG. 8, the image signal processor 270 may process the image signal 263 in accordance with the clock signal CLK generated from the pixel clock generator 150 to generate an image 271. The image signal processor 270 may include an amplifier 272, a sampler 274 and an image processor 276.

In particular, the amplifier 272 may amplify the image signal 263 outputted from the light detector 260 and output an amplified image signal 273 to the sampler 274. The sampler 274 may convert the amplified image signal 273 to a digital signal 275 in a specific frame time in synchronization with the clock signal CLK. The image processor 276 may image the digital signal per frame period to generate an image 271.

Figure 9:
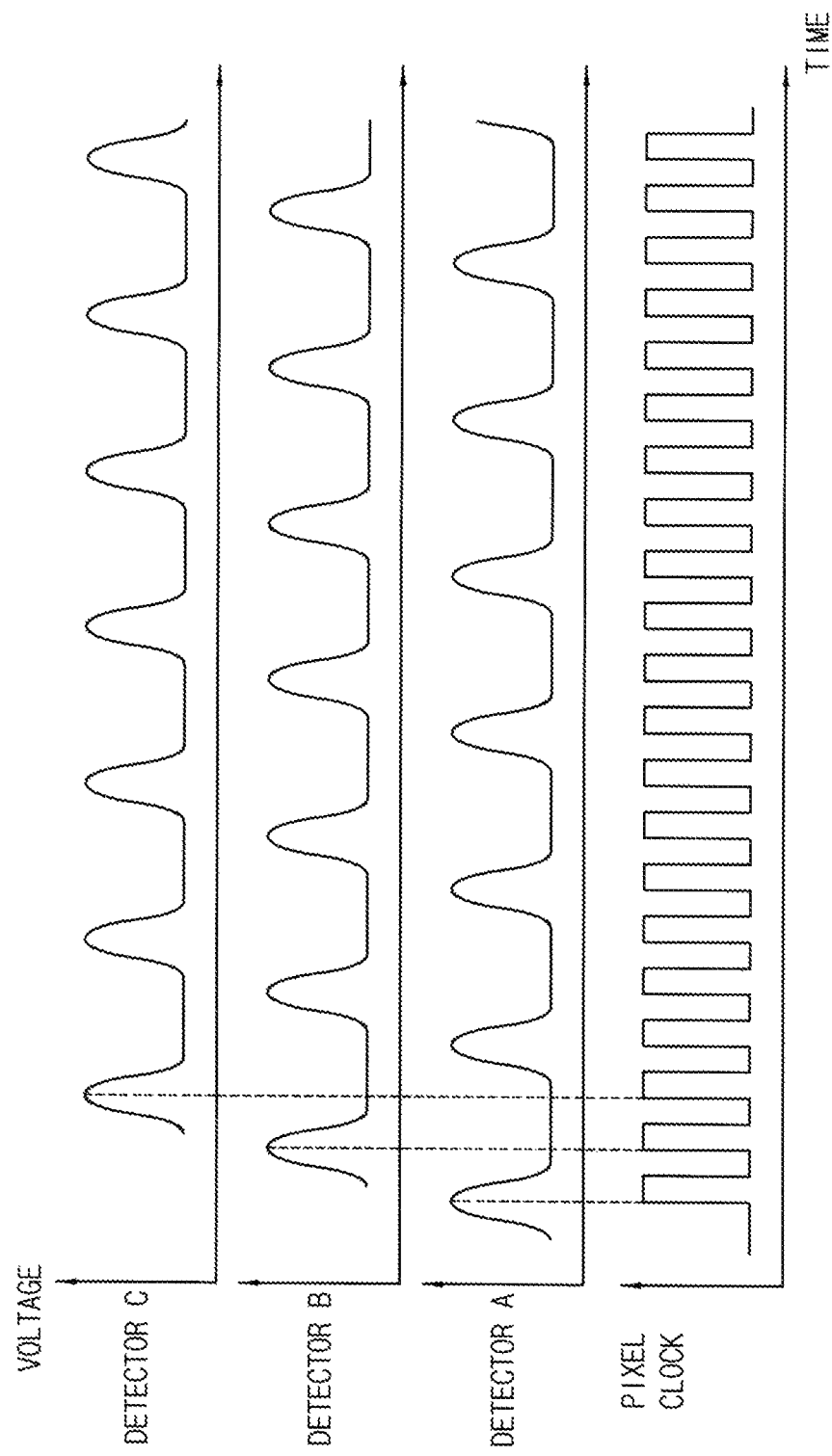

FIG. 9 includes graphs illustrating detection signals outputted from the light detector in FIG. 7 and a pixel clock signal generated by merging the detection signals.

Referring to FIG. 9, the first detection array 142A (DETECTOR A) may receive n first pulse signals during one scanning operation, the second detection array 142B (DETECTOR B) may receive n second pulse signals during the one scanning operation, and the third detection array 142C (DETECTOR C) may receive n third pulse signals during the one scanning operation.

Because each of the first to third pulse signals has an excellent signal contrast, the first to third digital signals may be generated based on the first to third pulse signals, respectively. The first to third digital signals may be merged into one channel signal to generate a clock signal CLK. The number of the pulses of the one channel clock signal CLK per one scanning operation (e.g., the frequency) may be 3n.

As mentioned above, the substrate inspecting apparatus 10 may use the optic mirror 120 as a galvano mirror to scan the light beam 211 on the semiconductor wafer W and detect a the light beam 261 reflected from the semiconductor wafer W and may generate an image from the detected reflected light beam 261. The substrate inspecting apparatus 10 may include a clock signal generator 100 which is configured to detect a rotation movement of the galvano mirror in real time and to generate a clock signal based on the measurement of the galvano mirror.

The clock signal generator 100 may include the grid plate 130 having one-dimensional grid arrays of N rows with regular gratings, which are offset by a same distance. The clock signal generator 100 may detect light passing through the grid arrays and combine the detected signals to finally generate a high-speed pixel clock signal.

Accordingly, image distortions due to nonlinear movement characteristics of the galvano mirror may be limited and/or prevented from occurring. Additionally, a plurality of the detection signals may be obtained from the grid arrays of N rows and the multi-channel parallel detection signals may be post-processed into one channel signal to generate the clock signal, thereby obtaining an image having an improved resolution. Further, a high-speed pixel clock signal may be generated even in the case that the pitch of the gratings is below a limit pitch of diffraction grating according to a wavelength of a laser beam.

Figure 10:
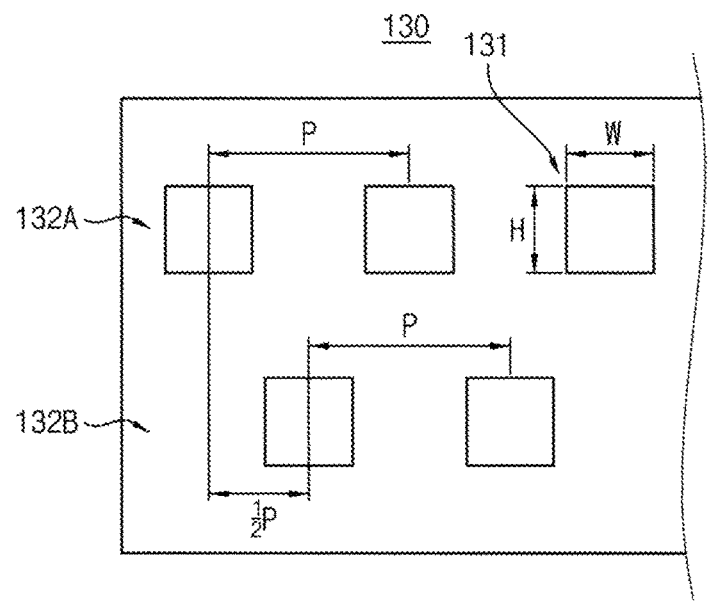
Figure 11:
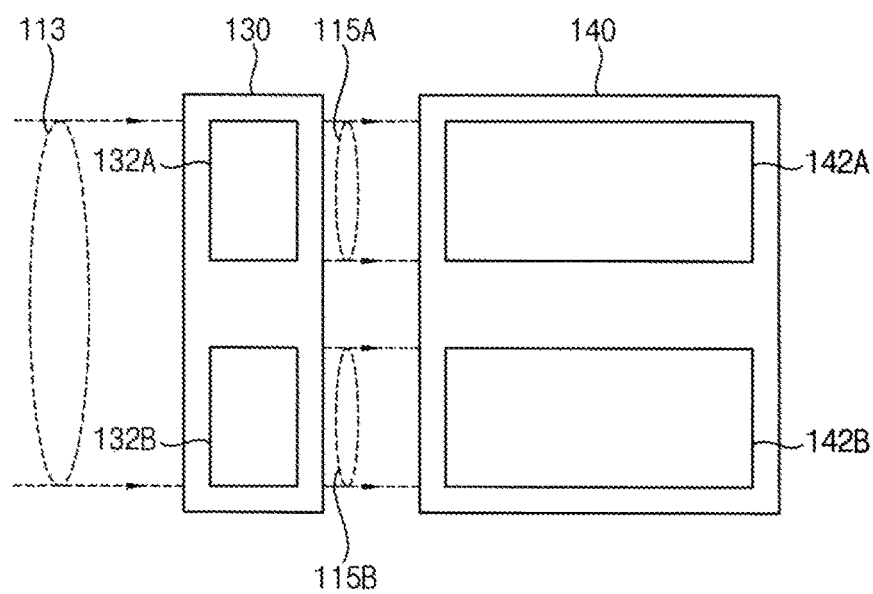

FIG. 10 is a plan view illustrating a grid plate 130 of a clock signal generator 100 in accordance with some example embodiments. FIG. 11 is a side view illustrating the grid plate 130 in FIG. 10 and a light detector 140. The clock signal generator 100 may be substantially the same as or similar to the clock signal generator 100 as described with reference to FIGS. 1 to 7, except for the number and an arrangement of grid arrays of the grid plate 130. Thus, same reference numerals will be used to refer to the same or like elements and any further repetitive explanation concerning the above elements will be omitted.

Referring to FIGS. 10 and 11, a grid plate 130 of a clock signal generator 100 may include two first and second grid arrays 132A and 132B arranged in a fourth direction (Z direction) perpendicular to a first direction (Y direction).

The first grid array 132A may include slits 131 arranged in the first direction (Y direction) to be spaced apart from one another. The second grid array 132B may include slits 131 arranged in the first direction (Y direction) to be spaced apart from one another. The pitch (P) of the first grid array 132A may be the same as the pitch (P) of the second grid array 132B. The second grid array 132B may be shifted by (½)*(P) with respect to the first grid array 132A.

As illustrated in FIG. 11, a light detector 140 may detect a beam 113 passing through the grid plate 130. The light detector 140 may include first and second detection arrays 142A and 142B to respectively detect light beams 115 passing through the first and second grid arrays 132A and 132B. The detection arrays 142A and 142B may include photodiodes.

The first detection array 142A may output a first voltage signal representing the intensity of the light passing through the first grid array 132A. The second detection array 142B may output a second voltage signal representing the intensity of the light passing through the second grid array 132B.

The clock signal generator may generate a clock signal (CLK) from the detected first and second voltage signals received from the light detector 140. Two parallel detection signals may be obtained through the grid arrays of two rows and may be merged into one channel signal to generate the clock signal (CLK), thereby obtaining an image having a two times improved resolution.

Figure 12:
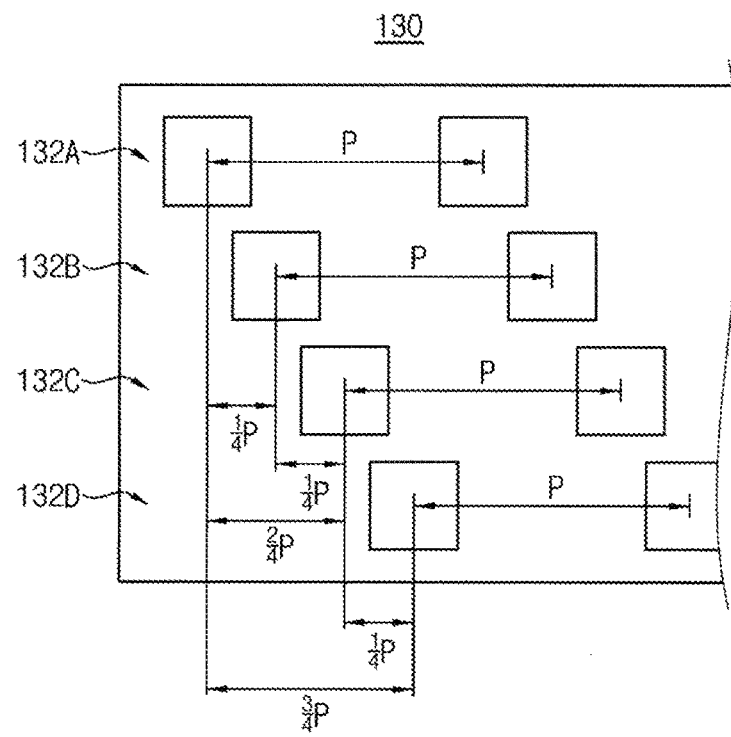
Figure 13:
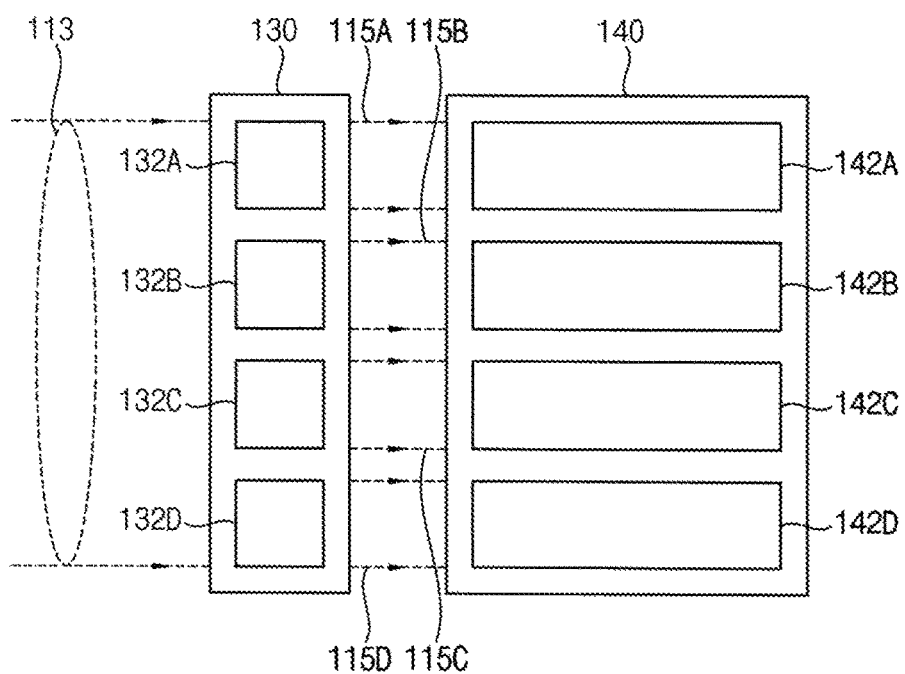

FIG. 12 is a plan view illustrating a grid plate 130 of a clock signal generator 100 in accordance with some example embodiments. FIG. 13 is a side view illustrating the grid plate 130 in FIG. 12 and a light detector 140. The clock signal generator 100 may be substantially the same as or similar to the clock signal generator 100 as described with reference to FIGS. 1 to 7, except for the number and an arrangement of grid arrays of the grid plate 130. Thus, same reference numerals will be used to refer to the same or like elements and any further repetitive explanation concerning the above elements will be omitted.

Referring to FIGS. 12 and 13, a grid plate 130 of a clock signal generator may include four first to fourth grid arrays 132A, 132B, 132C and 132D arranged in a fourth direction (Z direction) perpendicular to a first direction (Y direction).

The first grid array 132A may include slits 131 arranged in the first direction (Y direction) to be spaced apart from one another. The second grid array 132B may include slits 131 arranged in the first direction (Y direction) to be spaced apart from one another. The third grid array 132C may include slits 131 arranged in the first direction (Y direction) to be spaced apart from one another. The fourth grid array 132D may include slits 131 arranged in the first direction (Y direction) to be spaced apart from one another. The pitch (P) of the first grid array 132A may be the same as the pitch (P) of the second grid array 132B, the pitch (P) of the second grid array 132B may be the same as the pitch (P) of the third grid array 132B, the pitch (P) of the third grid array 132B may be the same as the pitch (P) of the fourth grid array 132D.

The second grid array 132B may be shifted by (¼)*(P) with respect to the first grid array 132A. The third grid array 132C may be shifted by (¼)*(P) with respect to the second grid array 132B. The fourth grid array 132D may be shifted by (¼)*(P) with respect to the third grid array 132A. The third grid array 132C may be shifted by (²⁄₄)*(P) with respect to the first grid array 132A. The fourth grid array 132D may be shifted by (¾)*(P) with respect to the first grid array 132A.

As illustrated in FIG. 13, a light detector 140 may detect a beam 113 passing through the grid plate 130. The light detector 140 may include first to fourth detection arrays 142A, 142B, 142C and 142D to respectively detect light beams 115A-D passing through the first to fourth grid arrays 132A, 132B, 132C and 132D. The detection arrays 132A, 132B, 132C and 132D may include photodiodes.

The first detection array 142A may output a first voltage signal representing the intensity of the light 115A passing through the first grid array 132A. The second detection array 142B may output a second voltage signal representing the intensity of the light 115B passing through the second grid array 132B. The third detection array 142C may output a third voltage signal representing the intensity of the light 115C passing through the third grid array 132C. The fourth detection array 142D may output a fourth voltage signal representing the intensity of the light 115D passing through the fourth grid array 132C.

The clock signal generator may generate a clock signal (CLK) from the detection signals received from the light detector 140. Four parallel detection signals may be obtained through the grid arrays of four rows and may be merged into one channel signal to generate the clock signal (CLK), thereby obtaining an image having a fourth times improved resolution.

Figure 14:
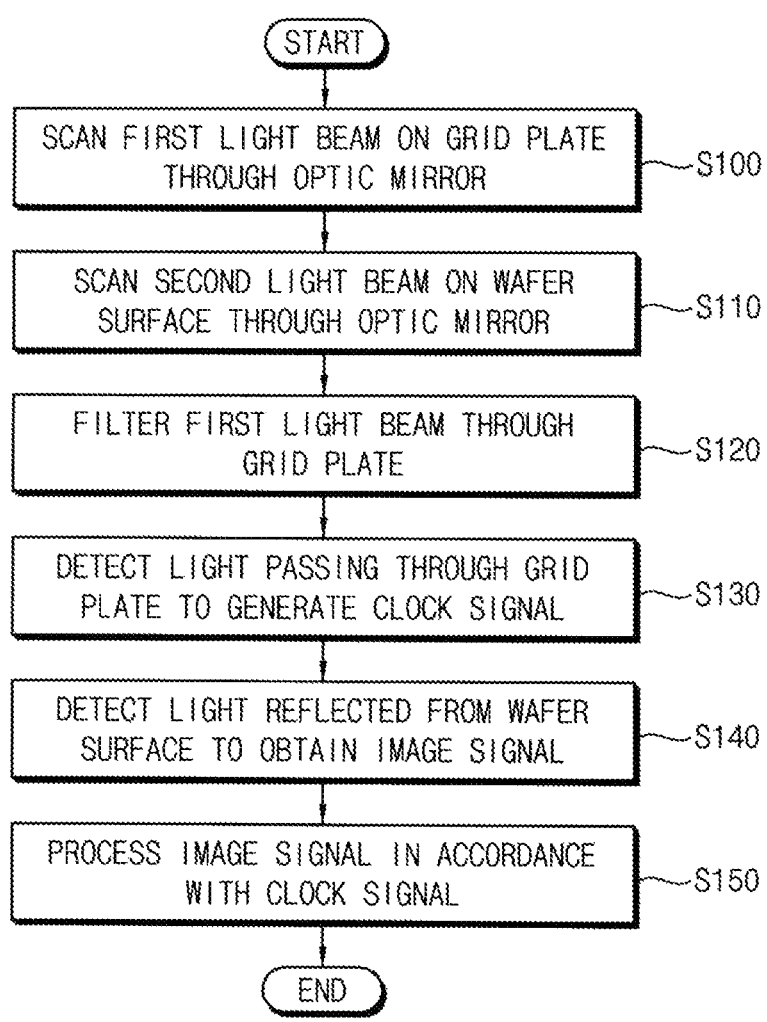

FIG. 14 is a flow chart illustrating a substrate inspecting method in accordance with some example embodiments.

Referring to FIGS. 1 and 14, first, a semiconductor wafer W may loaded onto a stage 300, and then, a first light beam as a clock signal generating light may be scanned on a grid plate 130 through an optic mirror 120 (S100) and a second light beam as an inspecting light may be scanned on a surface of the wafer W through the optic mirror 120 (S110).

The first light beam 111 generated from a first light source 110 of a clock signal generator 100 may be incident into a first reflective surface 122 of the optic mirror 120, and the second light beam 211 generated from a second light source 210 of an image generator 200 may be incident into a second reflective surface 124 of the optic mirror 120. The optic mirror 120 such as a galvano mirror may swing through a desired (or, alternatively, predetermined) angle to scan the first light beam 113 in Y direction on the grid plate 130 and scan the second light beam 211 in X direction on the wafer W.

The first light beam 111 may include a linear light beam as a linear light source. The light beam 113 scanning the grid plate 130 may include a linear light beam extending in Z direction. The light beam 113 reflected from the first reflective surface 122 of the optic mirror 120 may be condensed on the grid plate 130 by a condenser lens 114.

Then, the first light beam 113 may be filtered through a plurality of grid arrays of the grid plate 130 (S120).

The grid plate 130 may include a plurality of slits 131 through which the first light beam selectively passes when the first light beam is scanned in Y direction. The slits 131 may be arranged along Y direction, i.e., an extending direction of the grid plate 130, to be spaced apart from each other by a desired (or, alternatively, predetermined) pitch (P). The slits 131 may be arranged in rows parallel with Y direction respectively to form grid arrays of N rows (N is a natural number). Accordingly, the linear first light beam may be allowed to pass through or may be blocked by the gratings of the grid plate 130 depending on the position of the optic mirror 120.

Then, light passing through the grid arrays may be detected to generate a clock signal (S130).

A light detector 140 may detect a beam passing through the grid plate 130. The light detector 140 may include a plurality of detection arrays to respectively detect light passing through the grid arrays and output parallel detection signals. The detection arrays may include photodiodes.

A pixel clock generator 150 may convert the parallel detection signals received from the light detector 140 into digital signals respectively, and may merge a plurality of the parallel digital signals into one channel signal, to generate the clock signal.

Then, a light reflected from the surface of the wafer W may be detected to obtain an image signal (S140), and then, the image signal may be processed in accordance with the clock signal to generate an image with respect to the wafer W (S150).

The reflected beam from the surface of the semiconductor wafer W may be condensed on a light detector 260 through an objective lens 240, a relay lens 230, a polarizing mirror 220, a mirror 250 and a condenser lens 252. The light detector 260 may output an image signal in proportion to the intensity of the detected light. An image signal processor 270 may process the obtained image signal in a specific frame time in synchronization with the clock signal to generate an image.

As mentioned above, a rotation movement of the galvano mirror may be detected in real time and a clock signal may be generated based on the measurement of the position of the galvano mirror, to thereby limit and/or prevent image distortions due to nonlinear movement characteristics of the galvano mirror from occurring. Additionally, multi-channel parallel detection signals may be obtained through the grid arrays of N rows and then the multi-channel parallel detection signals may be post-processed into one channel signal to generate the clock signal, to thereby obtain an image having an improved resolution. Further, a high-speed pixel clock signal may be generated even in the case that the pitch of the gratings is below a limit pitch of diffraction grating according to a wavelength of a light beam.

It may be understood that the substrate inspecting apparatus and the substrate inspecting method according to example embodiments may be applicable to other substrates such as flat panel display (FPD), mask reticle for photomask, etc., besides a wafer.

The foregoing is illustrative of example embodiments and is not to be construed as limiting thereof. Although a few example embodiments have been described, those skilled in the art will readily appreciate that many modifications are possible in some example embodiments without materially departing from the novel teachings and advantages of the present example embodiments. Accordingly, all such modifications are intended to be included within the scope of example embodiments as defined in the claims.

What is claimed is:

1. A clock signal generator, comprising:
an optic mirror configured to be rotated and including a first reflective surface, the optic mirror configured to be rotated to cause the first reflective surface to scan a reflected first light beam in a first direction, the reflected first light beam being a linear laser beam having a cross section extending in a second direction different from the first direction;
a light source configured to generate the first light beam and direct the first light beam to the optic mirror;
a grid plate including a plurality of grid arrays, the plurality of grid arrays including N grid arrays, N being a natural number, arranged in the second direction, each grid array of the plurality of grid arrays configured to selectively pass a portion of the reflected first light beam reflected from the optic mirror therethrough when the optic mirror scans the first light beam on the grid plate in the first direction, each grid array including a plurality of slits spaced apart from each other by a particular pitch (P), each grid array being offset in the first direction by (1/N)*pitch (P) with respect to an adjacent grid array of the plurality of grid arrays, wherein the plurality of grid arrays are offset from each other in the second direction such that the linear laser beam of the reflected first light beam is simultaneously incident on each grid array of the plurality of grid arrays when the first reflective surface scans the reflected first light beam on the grid plate in the first direction;
a light detector configured to generate detection signals based on detecting portions of the reflected first light beam passing through the plurality of grid arrays; and
a pixel clock generator configured to generate a clock signal based on the detection signals.

2. The clock signal generator of claim 1, wherein a mth grid array (m=2, 3, . . . , N) of the plurality of grid arrays is offset by (1/N)*(P) with respect to a (m−1)th grid array of the plurality of grid arrays.

3. The clock signal generator of claim 1, wherein a mth grid array (m=2, 3, . . . , N) of the plurality of grid arrays is offset by ((m−1)/N)*(P) with respect to a first grid array of the plurality of grid arrays.

4. The clock signal generator of claim 1, wherein the second direction is substantially perpendicular to the first direction.

5. The clock signal generator of claim 1, wherein the optic mirror includes a galvano mirror having reflective surfaces on opposite sides.

6. The clock signal generator of claim 1, wherein the first light beam includes a linear laser beam having a cross section extending in the second direction.

7. A substrate inspecting apparatus, comprising:
a stage configured to support a substrate;
an optic mirror configured to be rotated and including a first reflective surface and a second reflective surface, the optic mirror configured to be rotated to cause the first reflective surface to scan a reflected first light beam in a first direction and to cause the second reflective surface to scan a reflected second light beam in a second direction on the substrate, the reflected first light beam being a linear laser beam having a cross section extending in a third direction different from the first direction;
a clock signal generator including,
a grid plate including a plurality of grid arrays arranged in the third direction, the grid arrays configured to selectively pass a portion of the reflected first light beam therethrough when the first reflective surface scans the reflected first light beam on the grid plate in the first direction, each grid array being offset in the first direction by a particular distance with respect to an adjacent grid array, wherein the plurality of grid arrays are offset from each other in the third direction such that the linear laser beam of the reflected first light beam is simultaneously incident on each grid array of the plurality of grid arrays when the first reflective surface scans the reflected first light beam on the grid plate in the first direction,
a light detector configured to generate detection signals based on detecting portions of the reflected first light beam passing through the grid arrays, and
a pixel clock generator configured to generate a clock signal based on the detection signals; and
an image generator configured to generate an image based on detection of the second light beam reflected from the substrate through the second reflective surface.

8. The substrate inspecting apparatus of claim 7, wherein the grid plate includes N grid arrays, N being a natural number, and the adjacent grid arrays are offset by (1/N) *pitch (P) to each other.

9. The substrate inspecting apparatus of claim 8, wherein a mth grid array (m=2, 3, . . . , N) of the plurality of grid arrays is offset by (1/N)*(P) with respect to a (m−1)th grid array of the plurality of grid arrays.

10. The substrate inspecting apparatus of claim 8, wherein a mth grid array (m=2, 3, . . . , N) of the plurality of grid arrays is offset by ((m−1)/N)*(P) with respect to a first grid array of the plurality of grid arrays.

11. The substrate inspecting apparatus of claim 7, wherein the third direction is substantially perpendicular to the first direction.

12. The substrate inspecting apparatus of claim 7, wherein the light detector includes a plurality of detection arrays configured to respectively detect light passing through the grid arrays.

13. The substrate inspecting apparatus of claim 12, wherein the pixel clock generator includes a synthesizer configured to merge parallel digital signals generated from the detection arrays to an individual channel signal to generate the clock signal.

14. The substrate inspecting apparatus of claim 7, wherein the image generator includes,
  a light detector configured to detect the second light beam reflected from the substrate to generate an image signal, and
  an image signal processor configured to process the image signal in accordance with the clock signal.

15. A clock signal generator, comprising:
  an optic mirror configured to be rotated to scan an incident first light beam in a first direction based on reflecting the first light beam, such that the reflected first light beam is a linear laser beam having a cross section extending in a second direction different from the first direction;
  a grid plate including a plurality of grid arrays offset from each other in the second direction, each grid array of the plurality of grid arrays extending in the first direction, each grid array, of the plurality of grid arrays, being offset in the first direction by a particular distance with respect to an adjacent grid array of the plurality of grid arrays, the grid plate configured to selectively direct at least a portion of the reflected first light beam through the grid plate when the optic mirror scans the reflected first light beam over the grid plate in the first direction, wherein the plurality of grid arrays are offset from each other in the second direction such that the linear laser beam of the reflected first light beam is simultaneously incident on each grid array of the plurality of grid arrays when the optic mirror scans the reflected first light beam over the grid plate in the first direction;
  a light detector configured to generate detection signals based on detecting portions of the reflected first light beam passing through the grid plate; and
  a pixel clock generator configured to generate a clock signal based on the detection signals.

16. The clock signal generator of claim 15, wherein at least one grid array of the plurality of grid arrays includes slits of a 1×n array, n being a positive integer number.

17. The clock signal generator of claim 15, wherein the light detector includes a plurality of detection arrays configured to respectively detect light passing through the grid arrays.

18. The clock signal generator of claim 17, wherein the pixel clock generator includes a synthesizer configured to merge parallel digital signals generated from the detection arrays to an individual channel signal to generate the clock signal.

* * * * *